United States Patent [19]

Voigtman et al.

[11] 4,413,504

[45] Nov. 8, 1983

[54] LIQUID-PHASE CHROMATOGRAPHY DETECTOR

[75] Inventors: Edward G. Voigtman; James D. Winefordner; Arthur R. Jurgensen, all of Gainesville, Fla.

[73] Assignee: University of Florida, Gainesville, Fla.

[21] Appl. No.: 382,633

[22] Filed: May 27, 1982

[51] Int. Cl.³ .................................................. G01N 31/06
[52] U.S. Cl. ............................... 73/61.1 C; 250/432 R
[58] Field of Search ................... 73/61.1 C; 250/423 P

[56] References Cited

U.S. PATENT DOCUMENTS

| | | | |
|---|---|---|---|
| 3,706,381 | 12/1972 | Joynes et al. | 73/61.1 C |
| 3,938,365 | 2/1976 | Dewey, Jr. | 73/24 |
| 3,997,298 | 12/1976 | McLafferty et al. | 73/61.1 C |
| 4,059,406 | 11/1977 | Fleet | 73/61.1 C |
| 4,170,736 | 10/1979 | Wessel | 250/423 P |
| 4,233,030 | 11/1980 | Twichett et al. | 73/61.1 C |

OTHER PUBLICATIONS

Malcolme-Lawes, Massey and Warwick, A Beta-Induced Fluorescence Detector, Jul. 1982.

*Primary Examiner*—Anthony V. Ciarlante
*Assistant Examiner*—Hezron Williams
*Attorney, Agent, or Firm*—Arthur G. Yeager

[57] ABSTRACT

A liquid-phase chromatography detector comprising a flow cell having an inlet tubular conduit for receiving a liquid chromatographic effluent and discharging it as a flowing columnar stream onto a vertically adjustable receiving surface spaced apart from and located vertically below and in close proximity to the discharge end of the tubular conduit; a receiver adapted to receive liquid overflowing from the receiving surface; an exit conduit for continuously removing liquid from the receiver; a light source for focussing fluorescence-producing light pulses on the flowing columnar stream as it passes from the outlet of the conduit to the receiving surface and a fluorescence detector to detect the produced fluorescence; a source of light pulse for producing acoustic waves in the columnar stream as it passes from the conduit outlet to the receiving surface; and a piezoelectric transducer adapted to detect those waves; and a source of bias voltage applied to the inlet tubular conduit and adapted to produce ionization of the liquid flowing through the flow cell so as to produce photocurrents therein and an electrical system to detect and record the photocurrents. This system is useful in separating and detecting individual chemical compounds from mixtures thereof.

19 Claims, 5 Drawing Figures

LIQUID-PHASE CHROMATOGRAPHY DETECTOR

U.S. GOVERNMENT SUPPORT

This invention was made with Government support under Contract DE-AS05-78OR06022 awarded by the Department of Energy and Grant GM11373 awarded by the National Institute of Health.

BACKGROUND OF THE INVENTION

Chromatography is a well-known analytical chemistry technique for identifying individual components in mixtures of component where ordinary methods of separation and identification are not feasible. Although the technique has been applied to mixtures of gases as well as to mixtures of liquids, the present invention relates solely to the latter, known as "liquid-phase" chromatography.

Various means of detecting different components in the liquid mixture are known based on the fact that different chemical compounds have different physical and chemical properties and characteristics. For example, the absorption of ultraviolet light or visible light, refractive index, heat of absorption, ionization, electrical conductivity, and fluoresence are properties upon which chromatographic analyses have been used. In each instance a cell is needed through which flows a small volume of liquid to be analyzed, and the cell must be equipped to provide means for detecting a property. In the present invention a flow cell is provided which is capable of detecting photoionization, photoacoustics, or fluorescence.

BRIEF SUMMARY OF THE INVENTION

One embodiment of this invention relates to a liquid-phase chromatography detector comprising a flow cell having an inlet tubular conduit for receiving a liquid chromatographic effluent and discharging it as a flowing columnar stream onto a vertically adjustable receiving surface spaced apart from the located vertically below and in close proximity to the discharge end of said conduit; a receiver adapted to receive liquid overflowing from said receiving surface; means for continuously removing liquid from said receiver; means for focussing fluorescence-producing light pulses on said flowing columnar stream as it passes from said conduit to said receiving surface and means to detect the produced fluorescence; means for focussing light pulses on said flowing columnar stream as it passes from said conduit to said receiving surface so as to produce acoustic waves in said stream and piezoelectric transducer means to detect those waves; and means to produce ionization of said liquid effluent passing through said flow cell so as to produce photocurrents therein and electrical means to detect said photocurrents.

Another embodiment of this invention relates to a windowless flow cell for use in liquid-phase chromatography comprising a hollow electrically insulating housing having an electrically conductive tube holder vertically adjustable therein by screw thread means and having an axial electrically conductive tubular conduit embedded therein, a vertically adjustable rod extending downwardly from a position in close proximity to the outlet of said tubular conduit through and beyond the bottom wall of said housing; a drainage conduit through a side wall of said housing adapted to conduct liquid away from a hollow of said housing around said rod; means to provide a bias voltage to the liquid flowing through said flow cell; an electrical connection to said rod outside said housing capable of transmitting a photocurrent signal to a recording means; and means for transmitting a photoacoustic signal from said rod including a quartz insulator disc bearing said rod and a piezoelectric disc bearing against said quartz disc.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawing in which:

DETAILED DESCRIPTION OF THE INVENTION

Liquid chromatography is widely used as an effective and efficient means of separating components in multi-component liquid phase mixtures. The system of this invention combines photoionization, photoacoustic, and fluorescence detection schemes for the detection of components in a liquid chromatographs's effluent. A cuvette flow cell is similar in basic design to the cell of this invention although sample volume of the cell of this invention is considerably smaller, i.e. less than 1 ml., and the cell walls are eliminated so as to avoid possible contamination and memory effects.

Figure 1:
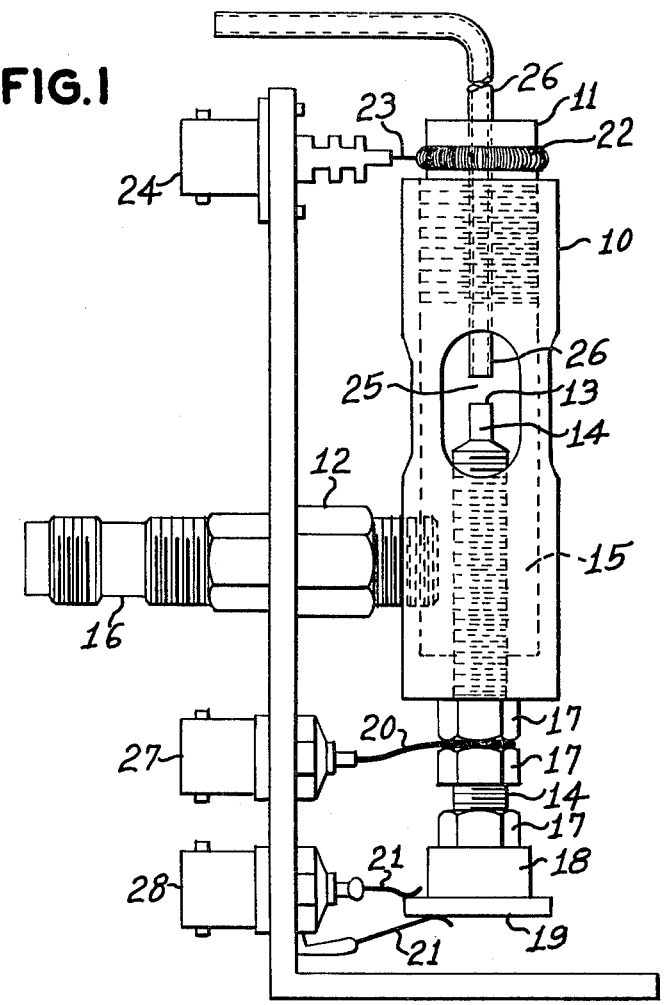
FIG. 1 is a front elevational view of the flow cell of this invention.

A windowless flow cell is provided for these purposes as shown in FIG. 1. Housing 10 is an electrically insulating, hollow, tubular member having internal threaded portions to electrically conductive, threaded tube holder 11 at the top of housing 10 and threaded rod 14 through the bottom of housing 10. Tube holder 11 contains a stainless steel tube 26, e.g. 0.063 O.D. and 0.020 I.D., passing through the cylindrical axis of tube holder 11. Effluent from a liquid chromatographic system enters tube 26 and exits immediately above surface 13 of rod 14 where surface tension of the liquid causes a column of the liquid to be suspended between tube 26 and surface 13. Rod 14 and tube holder 11 are both adjustable vertically by screw thread portions, so as to be positioned within about 0–4 mm., preferably about 2 mm., of each other. In that distance the liquid flowing from tube 26 onto surface 13 will, because of surface tension, form a small approximately cylindrical, flowing columnar stream of liquid through which chromatographic analyses may be made in accordance with this invention.

In the lower portion of housing 10 there is a receiver 15 for receiving liquid which overflows from surface 13 down the sides of rod 14 and is collected in receiver 15.

A liquid conduit 16 is joined to receiver 15 to drain the collected liquid away for disposal or use elsewhere.

In order to provide the three modes of detection of this invention there are provided means for introducing bias voltage at 24 and light through apertures 25 focussed on the column of liquid between tube 26 and surface 13. The detection of photocurrent produced by photoionization is a wire 20 conducting electric signals received from rod 14 to connector 27 to the detector recorder, not shown. The photoacoustic signal is received through rod 14 and transmitted through quartz insulator 18 to piezoelectric transducer disc 19 and conducting spring clips 21 to connector 28 to the detector recorder, not shown. Nuts 17 are adjusted on rod 14 to hold wire 20 and insulator 18 in proper positions. The bias voltage is produced by an external conventional power supply, e.g. a battery, and admitted through connector 24 and wire 23 to a coiled spring 22 encircling tube holder 11. A resistor of 10 million ohms may, if desired be placed between the power supply output voltage and connector 24 to avoid damage to the detector occasioned by short circuit conditions arising between tube 26 and surface 13.

The liquid chromatograph effluent solution passes through tube 26 and exits above surface 13 on rod 14. The draining liquid is supported by surface tension between tube 26 and surface 13 of rod 14 which preferably is made from a stainless steel ¼-20 threaded rod. The column of liquid is approximately cylindrical with a diameter of about 1-2 mm and height of about 1-2 mm. The flowing liquid exits the flow cell through receiver 15 to which is attached a stainless bulkhead union 12 and conduit 16, and from there into a waste bottle through e.g. polyethylene tubing. The average flow rate through such sized apparatus is about 1.5 ml./min. Tube 26, tube holder 11, rod 14, and conduit 16 are interconnected through housing 10, which preferably is made of polytetrafluoroethylene.

Tube 26 is positioned in and held in the polytetrafluoroethylene housing 10 by means of a conductive threaded tube holder 11, typically made of 30% by weight graphite-filled polytetrafluoroethylene and drilled along its cylindrical axis to admit stainless steel tube 26. In this way, the liquid chromatographic effluent solution may be raised to a bias voltage above or below ground potential while passing through the stainless steel tube 26. Since chromatographic systems are customarily operated at ground potential for safety reasons, it is essential that the liquid chromatographic effluent solution be conveyed from the chromatograph to the stainless steel tube 26 through an electrically insulating means, such as polytetrafluoraethylene tubing.

The flow cell has three modes of operation: fluorescence detection; photoacoustic detection; and photoionization detection. In the fluorescence mode, excitation light pulses are focussed in the center of the flowing liquid column through apertures 25 and fluorescence is observed at 90° to the excitation. No precautions, such as excitation and emission filters or polarizers are needed to lessen the effects of specular reflection since the emission monochromator provides sufficient rejection of interfering radiation.

In the photoacoustic mode, the incident light pulses generate acoustic waves in the liquid column. Such waves travel down the stainless steel rod 14 through a 1 cm thick quartz insulating disc 18, and into a piezoelectric transducer 19. The transducer output is amplified with a preamplifier.

Figure 2:
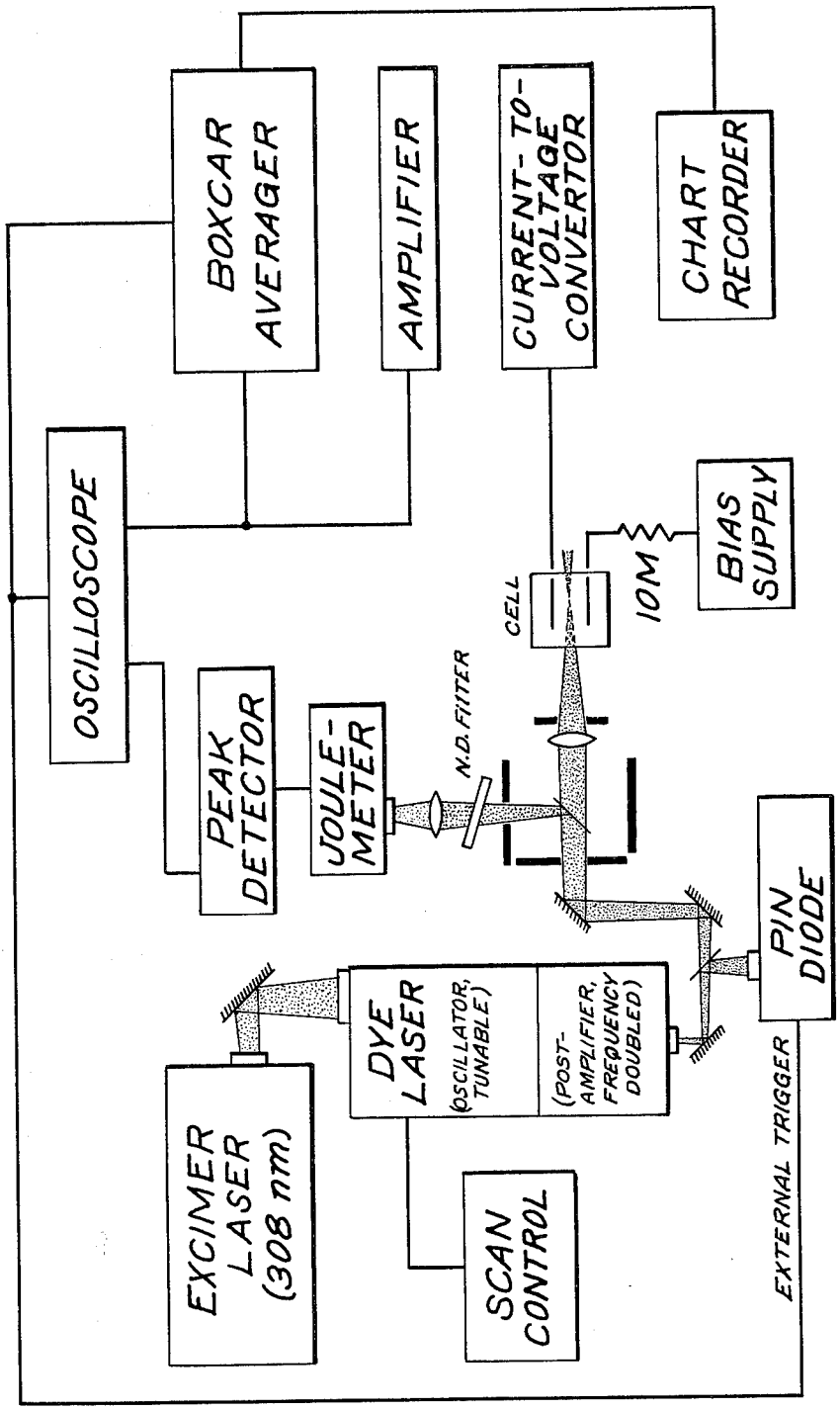
FIG. 2 is a schematic flow sheet of the detection system for photoionization employing the flow cell of this invention.

In the photoionization mode of operation, a bias voltage of $-10$ to $-5000$ volts is applied to tube 26 through coiled spring 22 connected through wire 23 to high voltage BNC connector 24, which, in turn, is connected through a 10 megohm current limiting resistor in series to the output of a commercial power supply source. Photocurrents due to two photon photoionization of the liquid being analyzed are collected at rod 14 and amplified with a current-to-voltage converter. The detection scheme for photoionization detection is shown in FIG. 2.

The following is exemplary of the operation of this system. The flow cell used was that of FIG. 1 wherein tube 26 was stainless steel with 0.063 O.D. and 0.020 I.D., and tube holder 11 was an inert, black, conductive coupling sleeve (1 inch long, 1/16 inch I.D., ⅜-18 outer threading) made of 30% (by wt.) graphite-filled polytetrafluoroethylene (PTFE) (Fluorocarbon, Anaheim, CA). Excitation illumination was provided by a Lumonics (Lumonics Research, Ontario, Canada) TE-861S excimer laser (XeCl, 308. nm, appx. 1 mJ/pulse, 20 Hz repetition rate) focussed onto the center of the flowing liquid column (appx. 6 uL suspended volume). The fluorescence (FL), photoacoustic (PA) and two-photon photoionization (PI) signals were acquired by approximate preamplifiers, amplifiers, and gated (boxcar) averager (PAR 160) with chart recorder output. The effluent from a high performance liquid chromatography (HPLC) system (Altex Scientific, Berkeley, CA, Model 312, 1.5 mL/min flow rate, isocratic operation, 4.6 mm×25 cm with Spherisorb ODS, 10 um packing, 20 uL sample injections) was passed to a commercial UV absorbance detector (Altex, Model 153, 254. nm) with chart recorder output and then through 0.6 m of narrow bore PTFE tubing to the stainless steel tubing 26 of the flow cell. The PTFE tubing isolated the bias voltage ($-1$ kV) on the flow cell from the grounded HPLC system. The DC leakage current that results from the use of the acetonitrile/water system was bypassed to ground through a 10 kiloohm metal film resistor while the pulsed PI current was passed to the preamplifier by a 50 nF, 1600 WV capacitor.

Bubble formation was avoided during this expermentation by bubbling the solvent mixture with He for at least an hour prior to the experiments. This resulted in shifts in the retention times of the compounds separated by HPLC. These shifts may be avoided by solvent programming. Electrolysis was not observed and electrode corrosion was negligible. Suitable materials for electrode construction include stainless steel, titanium, and graphite-filled PTFE. Laser excitation source focussing was found to be important, but not critical. The electrode gap was set by screwing tube holder 11 into housing 10 with a measured standard between the end of tube 26 and surface 13.

The organic compounds analyzed wre polynuclear aromatic hydrocarbons which were purchased commercially and were used without further purification as was acetonitrile employed.

A tabulation of limits of detection (LOD) for the fluorescence, photoionization, and photoacoustic modes with the flow cell of this invention is presented in Table 1. Five aromatic compounds are tested in 70/30 (vol./vol.) acetonitrile/water. The resultant LOD is fiben as micrograms/milliliter.

TABLE 1

Figure 3:
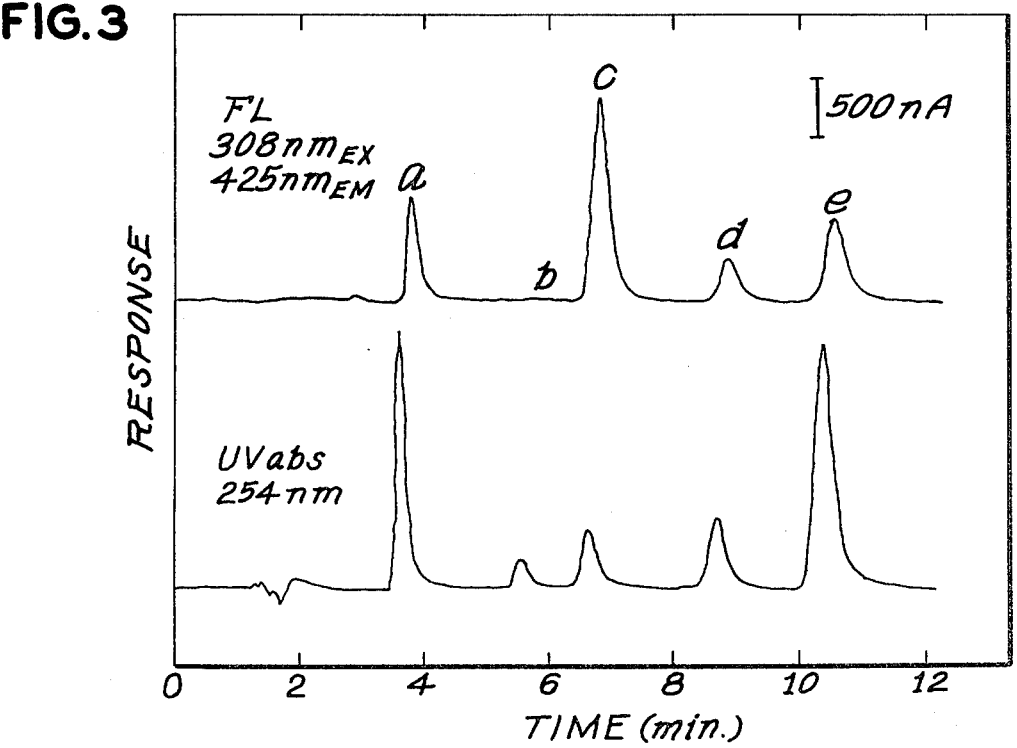
FIG. 3 is a chromatogram of test results employing the fluorescence mode of detection.
Figure 4:
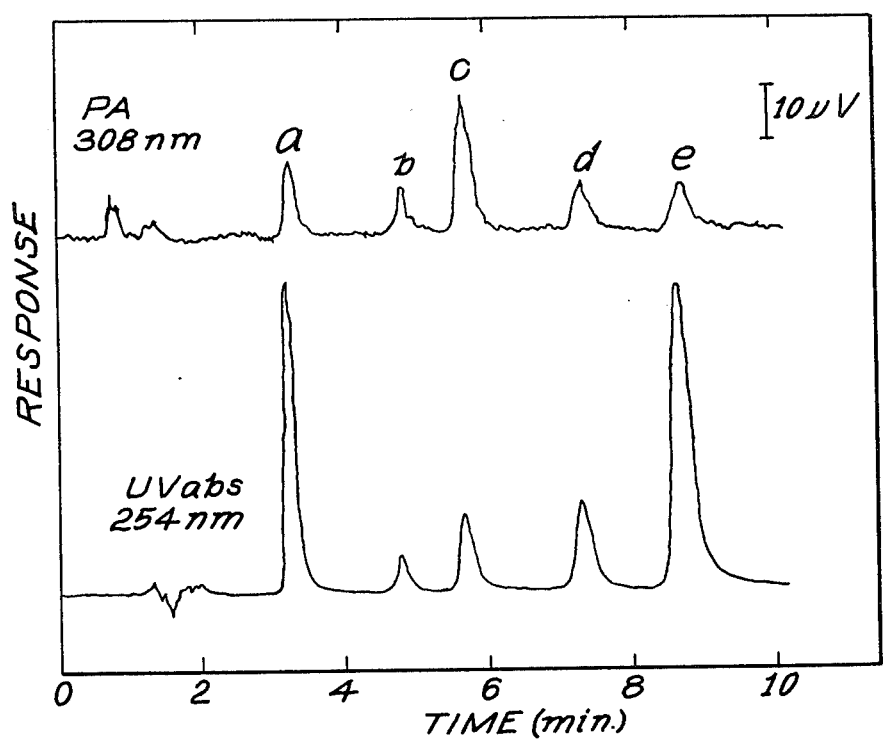
FIG. 4 is a chromatogram of test results employing the photoacoustic mode of detection.
Figure 5:
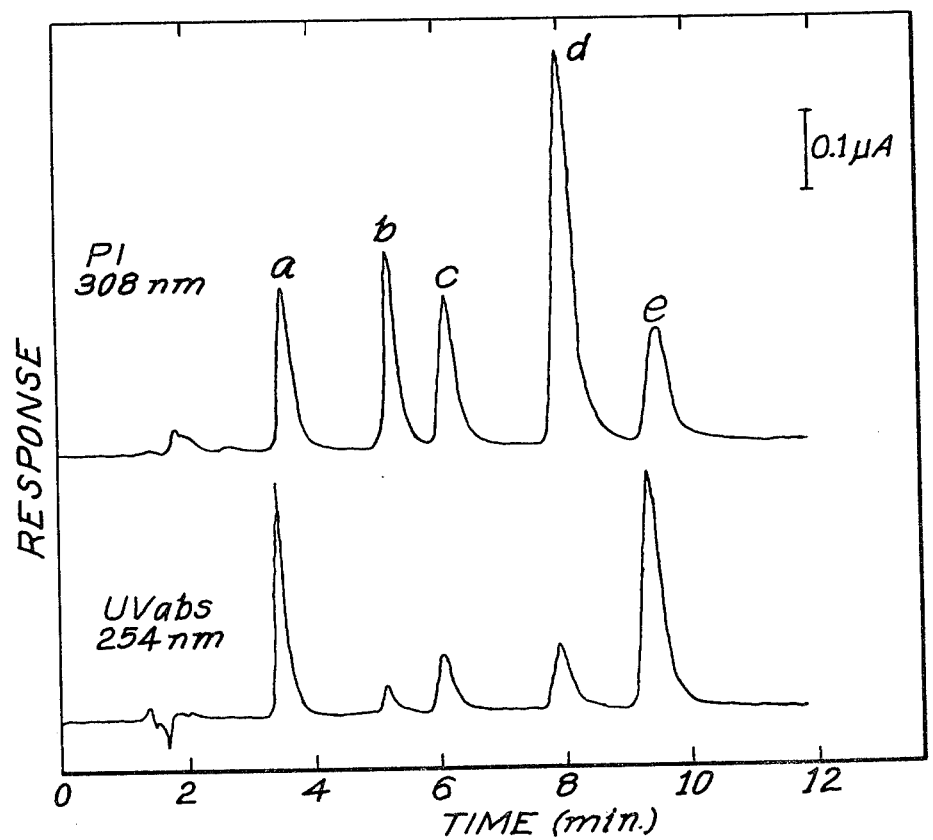
FIG. 5 is a chromatogram of test results employing the photoionization mode of detection.

| | \multicolumn{5}{c}{Chromatographic LOD (S/N = 3)} | | | | |
|---|---|---|---|---|---|
| | Acridine | Naphthalene | 7,8-benzo-flavone | N—ethyl-carbazole | Anthracene |
| UV absorbance | 0.05 | 0.4 | 0.2 | 0.2 | 0.02 |
| FL emission | 0.07 | 4. | 0.04 | 0.2 | 0.04 |
| PA | 4. | 7. | 2. | 8. | 3. |
| PI | 0.4 | 0.4 | 0.4 | 0.2 | 0.2 |
| Identification in FIGS. 3-5 | a | b | c | d | e |

The performances of the flow cell under actual operating conditions using the above materials and detection system are shown in FIGS. 3-5. FIG. 3 shows the fluorescence mode. FIG. 4 shows the photoacoustic mode. FIG. 5 shows the photoionization mode. In each instance there is also shown the conventional UV absorbance chromatogram. The liquid chromatograph effluent solution was first passed nondestructively through a commercial UV absorbance detector (Altex, Model 153, 254 nm, 0.005 sensitivity, i.e. maximum sensitivity) and then the solution was fed into the flow cell of this invention through tube 26 (FIG. 1) for detection by the modes of FIGS. 3, 4, and 5. The compounds of Table 1 were employed in these tests and are identified by letters a,b,c,d, and e as indicated.

The limits of detection by photoionization are substantially better than the photoacoustic results and somewhat poorer than the fluorescence results. This is partially explained by the fact that the compounds chosen for study are especially suitable for fluorescence detection.

The flow cell of this invention provides a sensitive detector for liquid chromatographic applications employing fluorescence, photoacoustic, and photoionization modes of operation. The advantage of such a detector is that photoacoustic detection is complementary to fluorescence detection and two photon photoionization detection is useful in quantitating substances which do not appreciably luminesce and which are relatively easily ionized.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A liquid-phase chromatography detector comprising a flow cell having an inlet tubular conduit for receiving a liquid chromatographic effluent and discharging it as a flowing columnar stream onto a vertically adjustable receiving surface spaced apart from and located vertically below and in close proximity to the discharge end of said conduit; a receiver adapted to receive liquid overflowing from said receiving surface; means for continuously removing liquid from said receiver; means for focussing fluorescence-producing light pulses on said flowing columnar stream as it passes from said conduit to said receiving surface and means to detect the produced fluorescence; means for focussing light pulses on said flowing columnar stream as it passes from said conduit to said receiving surface so as to produce acoustic waves in said stream and piezoelectric transducer means to detect those waves; and means to produce ionization of said liquid effluent passing through said flow cell so as to produce photocurrents therein and electrical means to detect said photocurrents.

2. The system of claim 1 wherein said receiving surface is vertically adjustable with respect to conduit so as to spaced apart from each other by a distance of 0-4 mm.

3. The system of claim 1 wherein said receiving surface is a horizontally flat end of a threaded bolt.

4. The system of claim 1 wherein said tubular conduit, said receiving surface, and said receiver are made of noncorroding, electrically conductive material.

5. The detector of claim 4 wherein said electrically conductive material is stainless steel.

6. The system of claim 1 wherein said light pulses comprise a laser beam.

7. The detector of claim 6 wherein said laser is a pulsed nitrogen laser.

8. The detector of claim 6 wherein said laser is a pulsed excimer laser.

9. The detector of claim 6 wherein said laser is a tunable dye laser.

10. The system of claim 1 wherein said means to produce ionization comprises the application of a bias voltage of −10 volts to −5000 volts through a 10-megohm resistor to a coiled spring encircling an electrically conductive, vertically adjustable tube holder having said tubular conduit embedded therein.

11. The system of claim 1 wherein said electrical means comprises two photon ionization spectroscopy.

12. A flow cell for use in liquid-phase chromatography comprising a hollow electrically insulating housing having an electrically conductive tube holder vertically adjustable therein by screw thread means and having an axial electrically conductive tubular conduit embedded therein, a vertically adjustable rod extending downwardly from a position in close proximity to the outlet of said tubular conduit through and beyond the bottom wall of said housing; a drainage conduit through a side wall of said housing adapted to conduct liquid away from a hollow of said housing around said rod, means to provide a bias voltage to the liquid flowing through said flow cell; an electrical connection to said rod outside said housing capable of transmitting a photocurrent signal to a recording means; and means for transmitting a photoacoustic signal from said rod including a quartz insulator disc bearing against said rod and a piezoelectric disc bearing against said quartz disc.

13. The cell of claim 12 wherein said housing is made of polytetrafluoroethylene and said conduit and said rod are made of stainless steel.

14. The cell of claim 12 wherein said tube holder has external threads to mate with internal threads in the top of said housing.

15. The cell of claim 12 wherein said conduit has a central passageway of about 0.02 inch in diameter.

16. The cell of claim 12 wherein said rod is a threaded bolt with a flat top surface that may be moved vertically so as to be positioned 0-4 mm. from the outlet of said conduit.

17. The cell of claim 12 wherein said housing is a hollow tube of polytetrafluoroethylene threaded internally at both ends and having a lateral threaded hole through the wall of said housing in the bottom portion of the housing.

18. The cell of claim 14 additionally comprising a coiled spring resistor of 10 megohm encircling the outside of said tube holder and connected to a source of −10 volts to −5000 volts bias voltage.

19. The cell of claim 12 having lateral apertures through the wall of said housing to permit a beam of light to be focussed on the space between the outlet of said conduit and the top of said rod and to pass beyond the housing.

* * * * *